United States Patent
Melvin

(10) Patent No.: US 6,221,103 B1
(45) Date of Patent: Apr. 24, 2001

(54) DEVICE AND METHOD FOR RESTRUCTURING HEART CHAMBER GEOMETRY

(75) Inventor: David B. Melvin, Loveland, OH (US)

(73) Assignee: The University of Cincinnati, Cincinnati, OH (US)

( * ) Notice: Subject to any disclaimer, the term of this patent is extended or adjusted under 35 U.S.C. 154(b) by 0 days.

(21) Appl. No.: 09/165,887

(22) Filed: Sep. 30, 1998

Related U.S. Application Data

(63) Continuation-in-part of application No. 08/581,914, filed on Jan. 2, 1996, now Pat. No. 5,957,977.

(51) Int. Cl.⁷ .......................................... A61F 2/00
(52) U.S. Cl. ............................................ 623/3.1; 623/3.11
(58) Field of Search ................................. 600/16–18, 37; 623/3.1, 3.11, 3.12, 3.16, 3.17

(56) References Cited

U.S. PATENT DOCUMENTS

| | | |
|---|---|---|
| 2,826,193 | 3/1958 | Vineberg . |
| 3,513,836 | 5/1970 | Sausse . |
| 3,668,708 | 6/1972 | Tindal . |
| 3,827,426 | 8/1974 | Page et al. . |
| 4,192,293 | 3/1980 | Asrican . |
| 4,621,617 | 11/1986 | Sharma . |
| 4,690,134 | 9/1987 | Snyders . |
| 4,809,676 * | 3/1989 | Freeman ............................... 600/16 |
| 4,936,857 | 6/1990 | Kulik . |
| 4,957,477 | 9/1990 | Lundback . |
| 5,131,905 | 7/1992 | Grooters . |
| 5,169,381 | 12/1992 | Snyders . |
| 5,192,314 | 3/1993 | Daskalakis . |
| 5,256,132 | 10/1993 | Snyders . |

(List continued on next page.)

FOREIGN PATENT DOCUMENTS

| | | |
|---|---|---|
| 0583012 | 2/1988 | (EP) . |
| WO9829041 | 7/1998 | (WO) . |
| WO 99/30647 | 6/1999 | (WO) . |
| WO 99/53977 | 10/1999 | (WO) . |
| WO 00/02500 | 1/2000 | (WO) . |
| WO 00/06026 | 2/2000 | (WO) . |
| WO 00/06027 | 2/2000 | (WO) . |
| WO 00/06028 | 2/2000 | (WO) . |
| WO 00/16700 | 3/2000 | (WO) . |

OTHER PUBLICATIONS

Melvin, D., "Ventricular Radius–Reduction Without Resection: A Computational Assessment," *ASAIO Journal* (Abstract), vol. 44, No. 2, p. 57A, Mar. 5, 1998.

(List continued on next page.)

*Primary Examiner*—Michael J. Milano
(74) *Attorney, Agent, or Firm*—Ratner & Prestia

(57) ABSTRACT

A geometric reconfiguration assembly for the natural heart having a collar configured for surrounding the natural heart. The collar can include a plurality of bands, such as thin bands of about 0.2 mm in thickness, in a spaced relationship to each other, and a connector bar intersecting the plurality of bands and configured for maintaining the spaced relationship of the bands to each other. The collar may include a plurality of bands, such as from about 2 to about 10 bands, that are positioned parallel to each other. The bands can each be made of a biomedical material, such as polyacetal or a metal, such as titanium or steel.

The connector bar of the present invention can be positioned tangential to the plurality of bands, and may have a plurality of grooves configured to receive the thickness of each of the plurality of bands. The grooves also may be beveled to allow for the bands to flex as the heart beats. The connector bar's inner surface can have an outwardly convex curved configuration, and may even include a cushioned portion that can be made from a polymeric material. A pad may be positioned between the collar and the epicardial surface of the heart that may comprise a low durometer polymer, or either a gel-filled cushion or a fluid-filled cushion.

24 Claims, 10 Drawing Sheets

U.S. PATENT DOCUMENTS

| | | |
|---|---|---|
| 5,345,949 | 9/1994 | Shlain . |
| 5,383,840 | 1/1995 | Heilman et al. . |
| 5,385,528 * | 1/1995 | Wilk ............................................ 600/18 |
| 5,484,391 | 1/1996 | Buckman, Jr. et al. . |
| 5,571,176 * | 11/1996 | Taheri ........................................ 623/3 |
| 5,702,343 | 12/1997 | Alferness . |
| 5,709,695 | 1/1998 | Northrup, III . |
| 5,713,954 | 2/1998 | Rosenberg et al. . |
| 5,738,626 * | 4/1998 | Jarvik ........................................ 606/16 |
| 5,738,627 * | 4/1998 | Kovaks et al. ............................ 600/16 |
| 5,749,883 | 5/1998 | Halpern . |
| 5,800,528 * | 9/1998 | Lederman et al. ........................ 623/3 |
| 5,961,440 * | 10/1999 | Schweich, Jr. et al. ................. 600/16 |
| 6,019,722 * | 2/2000 | Spence et al. ........................... 600/210 |
| 6,045,497 | 4/2000 | Schwiech, Jr. et al. . |
| 6,050,936 | 4/2000 | Schwiech, Jr. et al. . |
| 6,059,715 | 5/2000 | Schwiech, Jr. et al. . |
| 6,077,214 | 6/2000 | Mortier et al. . |

OTHER PUBLICATIONS

Melvin, D., "Ventricular Radius–Reduction Without Resection: A Computational Assessment," *ASAIO Annual Meeting*(Poster), Jun., 1998.

Melvin, D. B.; Melvin, A.J.; Trossman, C.A.; and Glos, D.L., "Reduction of Ventricular Wall Tensile Stress by Geometric Remodeling Device," *ASAIO Journal* (Abstract), vol. 45, No. 2, p. 166, Mar. 17, 1999.

Melvin, D.B.; Melvin, A.J.; Trossman, C.A.; and Glos, D.L., "Reduction of Ventricular Wall Tensile Stress by Geometric Remodeling Device," *ASAIO Annual Meeting*(Poster), Jun., 1999.

Boyer, Mike, "SDRC Agreement Could Hasten Medical Advances, "The Cincinnati Enquirer, Mar. 2, 1999.

Miller, Nick, "SDRC gives its software to BIO/START," *The Cincinnati Post*, Mar. 2, 1999.

Bonfield, Tim, "CardioClasp may help biomedical," *The Cincinnati Enquirer*, Nov. 7, 1999.

Bonfield, Tim, "Surgeon's invention could help thousands—Tests begin on device to treat heart disease," *The Cincinnati Enquirer*, Sunday, Nov. 7, 1999.

Vaccariello, Linda, "Who Will Invent the Cures?," *Cincinnati*, Dec. 1999, p. 64.

SDRC Agreement to Speed Medical Advances,: *University of Cincinnati News & Info*, Apr. 1999 Newsletter.

Tellides et al, *Journal of Heart and Lung Transplantation*, (1998)17:1, Abstract No. 180, p. 89.

Kawaguchi et al, *Journal of Heart and Lung Transplantation*, (1998)17:1, Abstract No. 181, p. 89.

Dowling et al, *Journal of Heart and Lung Transplantation*, (1998)17:1, Abstract No. 76, p. 62.

Khoynezhad et al, *Journal of Heart and Lung Transplantation*, (1998)17:1, Abstract No. 77, p. 62.

Batista et al, *Ann. Thorac. Surg.*, (1997)64, pp. 634–638.

* cited by examiner

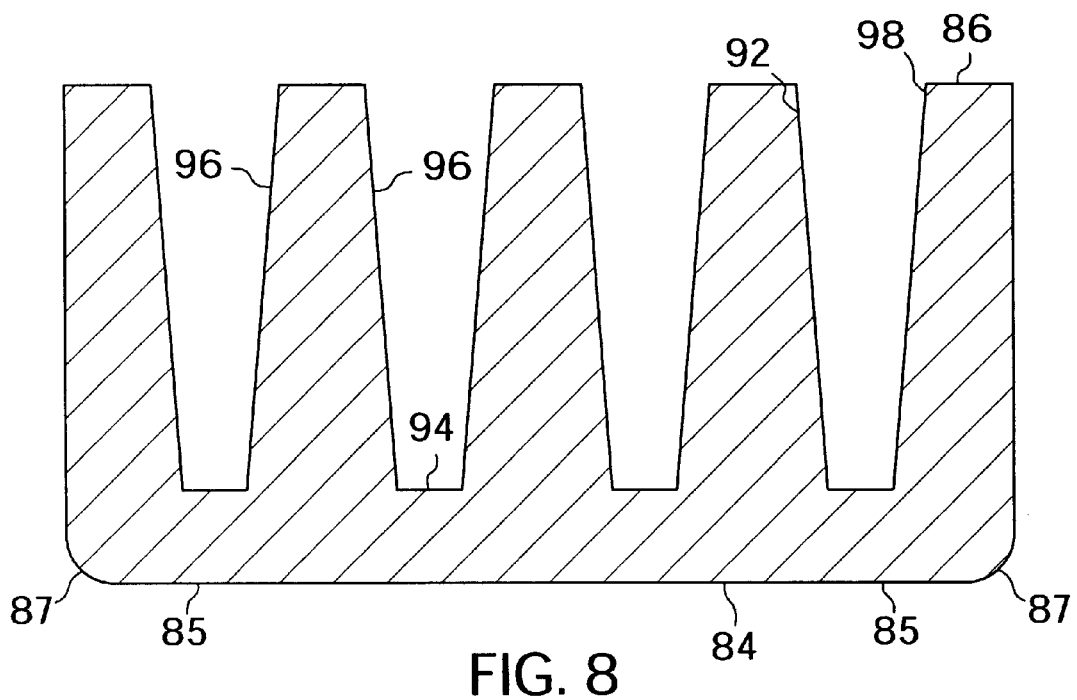
FIG. 8
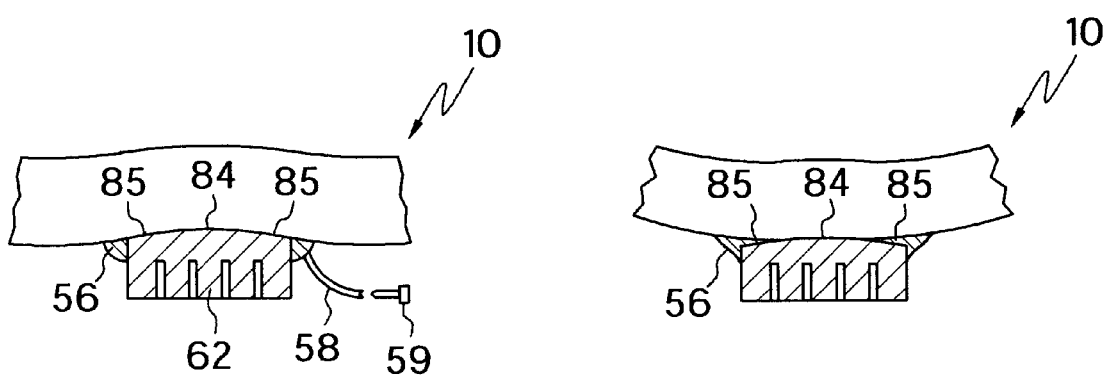
FIG. 9A
FIG. 9B

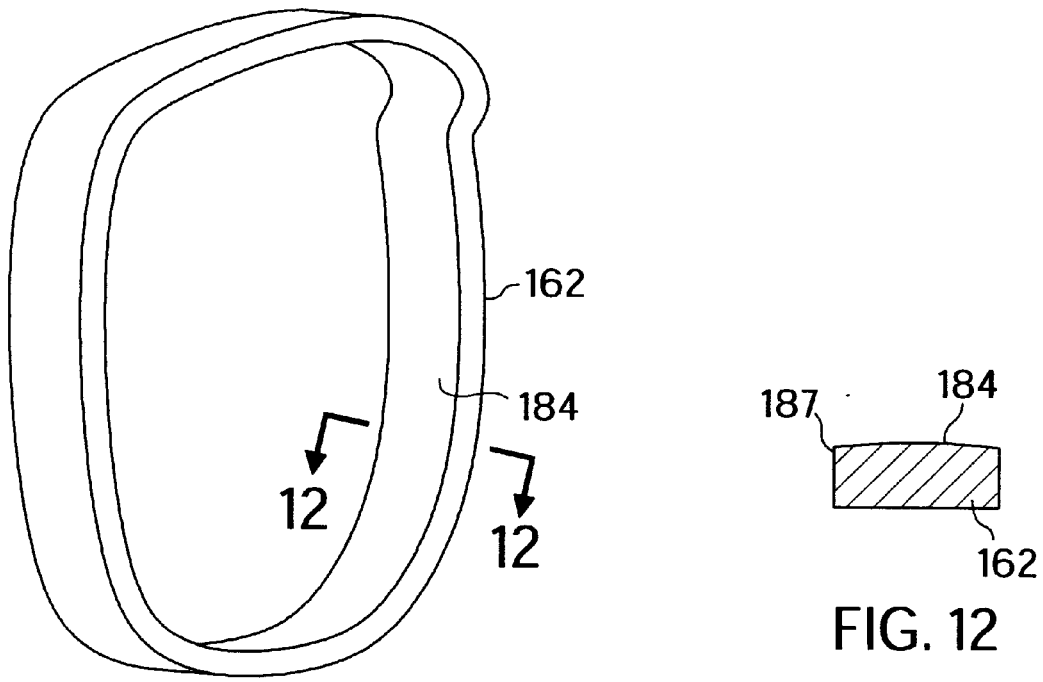
FIG. 11
FIG. 12
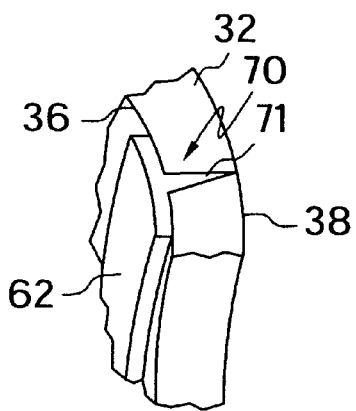
FIG. 16a
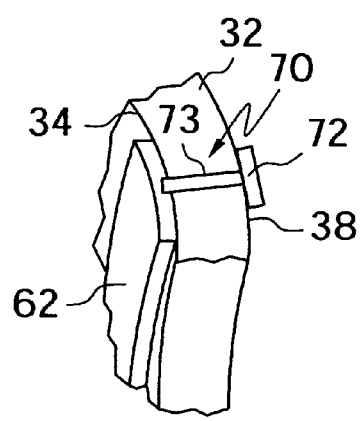
FIG. 16b

DEVICE AND METHOD FOR RESTRUCTURING HEART CHAMBER GEOMETRY

REFERENCE TO COPENDING APPLICATION

This is a continuation in part application of United States patent application Ser. No. 08/581,914, filed Jan. 2, 1996, entitled "Activation Device for the Natural Heart and Method of Doing the Same," now U.S. Pat. No. 5,957,977.

TECHNICAL FIELD OF THE INVENTION

The present invention relates to a device and method for treating cardiomyopathies and/or enlarged hearts and more specifically, a device and method for decreasing a heart chamber's wall tension.

BACKGROUND OF THE INVENTION

The natural heart, and specifically, the cardiac muscle tissue of the natural heart (e.g., myocardium) can fail for various reasons to a point where the natural heart cannot provide sufficient circulation of blood for a body so that life can be maintained. More specifically, the heart and its chambers can become enlarged for a variety of causes and/or reasons, including viral disease, idiopathic disease, valvular disease (mitral, aortic and/or both), ischemic disease, Chagas' disease and so forth. As the heart and its chambers enlarge, tension of the walls of the heart's chambers increase and thus, the heart must develop more wall tensile stress to generate the needed pressure for pumping blood through the circulatory system. The process of ventricular dilation is generally the result of chronic volume overload or specific damage to the myocardium. In a normal heart that is exposed to long-term increased cardiac output requirements, for example, for an athlete, there is an adaptive process of slight ventricular dilation and muscle myocyte hypertrophy. In this way, the heart may fully compensate for the increased cardiac output requirements of the body. With damage to myocardium or chronic volume overload, however, there are increased requirements put on the contracting myocardium to such a level that this compensated state is never achieved and the heart continues to dilate.

A problem with an untreated dilated ventricle is that there is a significant increase in wall tension and/or stress, both during the diastolic filling, and during the systolic contraction. In a normal heart, the adaption of muscle hypertrophy (e.g. thickening) in the ventricular dilation maintains a fairly constant wall tension for systolic constriction. However, in a failing heart, the ongoing dilation is greater than the hypertrophy, and as a result, rising wall tension is required for systolic contraction. This is believed to result in further muscle damage.

The increase in wall stress is also true for diastolic filling. Additionally, because of the lack of cardiac output, ventricular filling pressure tends to rise due to several physiologic mechanisms. Moreover, in diastole, both the diameter and wall pressure increase over normal levels, thus contributing to higher wall stress levels. As a solution for the enlarged natural heart, attempts have been made in the past to provide a treatment to maintain circulation. Prior treatment for heart failure generally fall into three categories, namely surgical treatments; mechanical support systems; or pharmacological.

One such approach has been to replace the existing natural heart in a patient with an artificial heart or a ventricular assist device. In using artificial hearts and/or assist devices, a particular problem stems from the fact that the materials used for the interior lining of the chambers of an artificial heart are in direct contact with the circulating blood, which can enhance undesirable clotting of the blood, build up of calcium, or otherwise inhibit the blood's normal function. Hence, thromboembolism and hemolysis could occur with greater ease. Additionally, the lining of an artificial heart or a ventricular assist device can crack, which inhibits performance, even if the crack is at a microscopic level. Moreover, these devices must be powered by a source which can be cumbersome and/or external to the body. Drawbacks have limited use of these devices to applications having too brief a time period to provide a real lasting benefit.

An alternative procedure is to transplant a heart from another human or animal into a patient. The transplant procedure requires removing an existing organ (i.e., the natural heart) for substitution with another organ (i.e., another natural heart) from another human, or potentially, from an animal. Before replacing an existing organ with another, the substitute organ must be "matched" to the recipient, which can be, at best, difficult and time consuming to accomplish. Furthermore, even if the transplanted organ matches the recipient, a risk exists that the recipient's body will reject the transplanted organ and attack it as a foreign object. Moreover, the number of potential donor hearts is far less than the number of patients in need of a transplant. Although use of animal hearts would lessen the problem with fewer donors than recipients, there is an enhanced concern with rejection of the animal heart.

In an effort to use the existing natural heart of a patient, other attempts have been made to reduce wall tension of the heart by removing a portion of the heart wall, such as a portion of the left ventricle in a partial left ventriculectomy procedure (the Batista procedure). A wedge-shaped portion of the ventricular muscle has been removed, which extends from the apex to the base of the heart. By reducing the chamber's volume, and thus its radius, the tension of the chamber's wall is reduced as well. There are, however, several drawbacks with such a procedure. First, a valve (i.e., the mitral valve) may need to be repaired or replaced depending on the amount of cardiac muscle tissue to be removed. Second, the procedure is invasive and traumatic to the patient. As such, blood loss and bleeding can be substantial during and after the procedure. Moreover, as can be appreciated by those skilled in the industry, the procedure is not reversible.

Another device developed for use with an existing heart for sustaining the circulatory function of a living being and the pumping action of the natural heart is an external bypass system, such as a cardiopulmonary (heart-lung) machine. Typically, bypass systems of this type are complex and large, and, as such, are limited to short term use in an operating room during surgery, or to maintaining the circulation of a patient while awaiting receipt of a transplant heart. The size and complexity effectively prohibit use of bypass systems as a long term solution, as they are rarely even portable devices. Furthermore, long term use of these systems can damage the blood cells and blood borne products, resulting in post surgical complications such as bleeding, thromboembolism function, and increased risk of infection.

Medicines have been used to assist in treating cardiomyopathies. Some inotropic agents can stimulate cardiac work. For example, digoxin can increase the contractibility of the heart, and thereby enhances emptying of the chambers during systolic pumping. Medicines, such as diuretics or vasodilators attempt to reduce or decrease the heart's work-load. For example, indirect vasodilators, such as angiotensin-converting enzyme inhibitors (e.g., enalopril), can help reduce the tendency of the heart to dilate under the increased diastolic pressure experienced when the contractibility of the heart muscle decreases. Many of these medicines have side effects, such as excessive lowering of blood pressure, which make them undesirable for long term therapy.

As can be seen, currently available treatments, procedures, medicines, and devices for treating end-stage cardiomyopathies have a number of shortcomings that contribute to the complexity of the procedure or device. The current procedures and therapies can be extremely invasive, only provide a benefit for a brief period of time, or have undesirable side effects which can hamper the heart's effectiveness. There exists a need in the industry for a device and procedure that can use the existing heart to provide a practical, long-term therapy to reduce wall tension of the heart, and thus improve its pumping efficiency.

SUMMARY OF THE PRESENT INVENTION

It is the object of the present invention to provide a device and method for treating cardiomyopathies that addresses and overcomes the above-mentioned problems and shortcomings in the thoracic medicine art.

It is another object of the present invention to provide a device and method for treating cardiomyopathies that minimizes damage to the coronary circulatory and the endocardium.

It is still a further object of the present invention to provide a device and method for treating cardiomyopathies that maintains the stroke volume of the heart.

Another object of the present invention is to provide a device and method for treating cardiomyopathies that supports and maintains the competence of the heart valves so that the heart valves can function as intended.

Still another object of the present invention is to provide a device and method that increases the pumping effectiveness of the heart.

Yet another object of the present invention is to provide a device and method for treating cardiomyopathies on a long term basis.

It is yet still an object of the present invention to provide a device and method for treating cardiomyopathies that does not require removal of any portion of an existing natural heart.

Still a further object of the present invention is to provide a device and method for treating dilated cardiomyopathies that directly reduce the effective radius of a chamber of a heart in systole as well as in diastole.

Additional objects, advantages, and other features of the present invention will be set forth and will become apparent to those skilled in the art upon examination of the following, or may be learned with practice of the invention.

To achieve the foregoing, a geometric reconfiguration assembly is provided for the natural heart having a collar configured for surrounding the natural heart. The collar can include a plurality of bands, such as thin bands of about 0.2 mm in thickness, in a spaced relationship to each other, and a connector bar intersecting the plurality of bands and configured for maintaining the spaced relationship of the bands to each other. The collar may include a plurality of bands, such as from about 2 to about 10 bands, that are positioned parallel to each other. The bands can each be made of a biomedical material, such as polyacetal or a metal, such as titanium or steel.

The connector bar of the present invention can be positioned tangential to the plurality of bands, and may have a plurality of grooves configured to receive the thickness of each of the plurality of bands. The grooves also may be beveled to allow for the bands to flex as the heart beats. The connector bar's inner surface can have an outwardly convex curved configuration, and may even include a cushioned portion that can be made from a polymeric material. A pad may be positioned between the collar and the epicardial surface of the heart that may comprise a low durometer polymer, or either a gel-fiiled cushion or a fluid-filled cushion.

The assembly of the present invention may also comprise a closure device for enclosing at least one of the bands in the connector bar.

In use, the present invention can reduce the wall tension on one of the chambers of the heart. A yoke or collar surrounds the heart so as to provide the chamber of the heart as at least two contiguous communicating regions, such as sections of truncated ellipsoids, which have a lesser minimum radii than the chamber before restructuring. As such, the collar displaces at least two portions of the chamber wall inwardly from the unrestricted position.

BRIEF DESCRIPTION OF THE DRAWINGS

While the specification concludes with claims particularly pointing out and distinctly claiming the present invention, it is believed the same will be better understood from the following description taken in conjunction with the accompanied drawings in which:

FIG. 8 is a cross sectional view of a connector of the present invention taken along line 8—8 in FIG. 7;

FIG. 9A is a partial horizontal cross sectional view of an assembly made in accordance with the present invention while the heart is at rest;

FIG. 9B is a partial horizontal cross sectional view of an assembly made in accordance with the present invention while the heart is contracting:

FIG. 11 is an alternative embodiment ofthe assembly made in accordance with the present invention;

FIG. 12 is a cross sectional view of one embodiment of the collar of the present invention taken along line 12—12 in FIG. 11;

FIGS. 16a and 16b are partial perspective views of two embodiments of auxiliary connectors made in accordance with the present invention;

DETAILED DESCRIPTION OF THE PREFERRED EMBODIMENT

Figure 1:
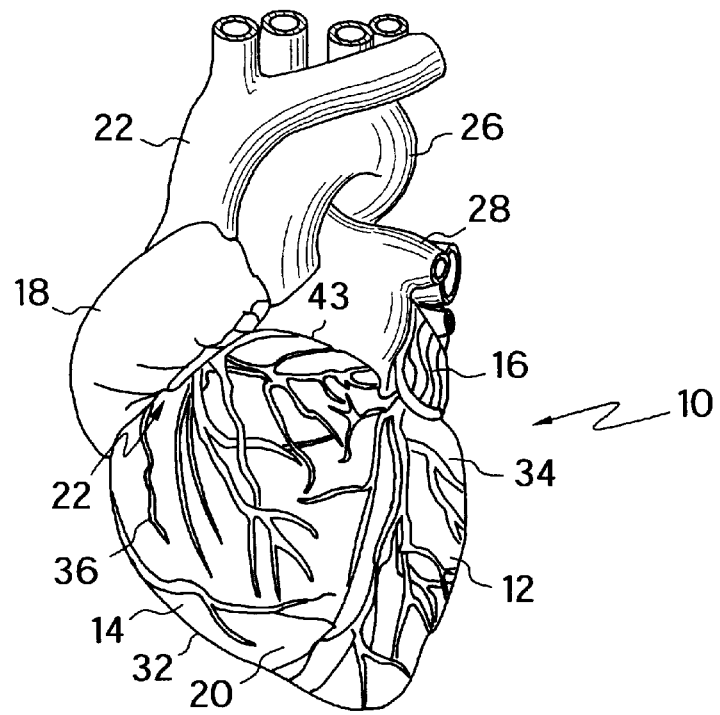
FIG. 1 is a partial frontal anterior view of an exemplar natural heart.
Figure 2:
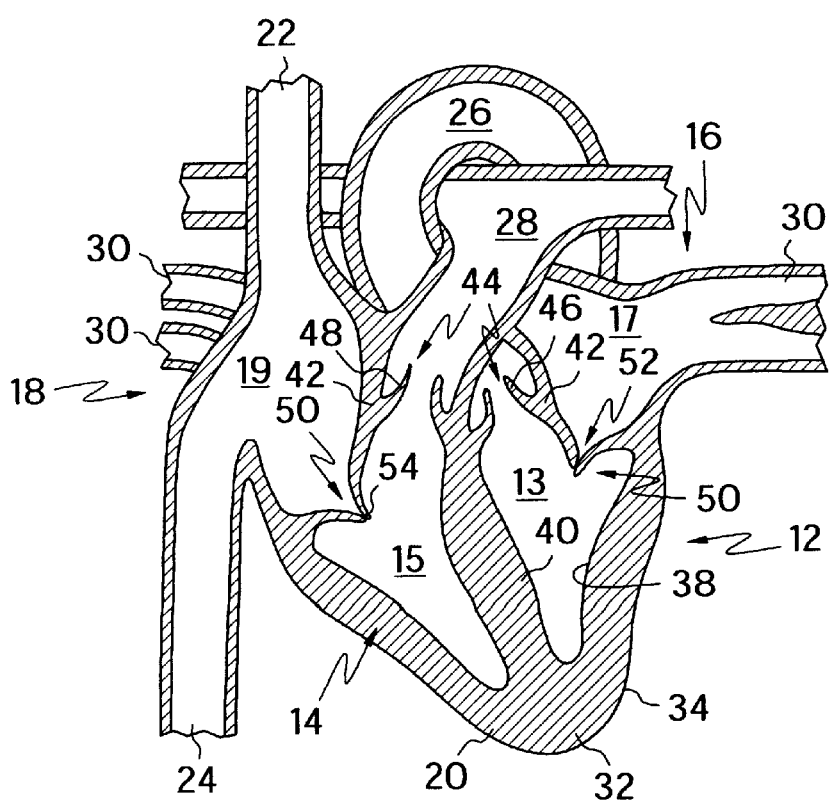
FIG. 2 is a vertical cross sectional view of an exemplar natural heart and blood vessels leading to and from the natural heart.

Referring now to the figures in detail wherein like numerals indicate the same elements throughout the views, an exemplary natural heart, generally indicated in FIGS. 1 and 2 as 10, has a lower portion comprising two chambers, namely a left ventricle 12 and a right ventricle 14, which finction primarily to supply the main force that propels blood through the circulatory system, namely the pulmonary circulatory system, which propels blood to and from the lungs, and the peripheral circulatory system, which propels blood through the remainder of the body. A natural heart 10 also includes an upper portion having two chambers, a left atrium 16 and a right atrium 18, which primarily serve as an entryway to the left and right ventricles 12 and 14, respectively, and assist in moving blood into the left and right ventricles 12 or 14. The interventricular wall 40 of cardiac tissue 32 separates the left and right ventricles 12 and 14, and the atrioventricular wall 42 of cardiac tissue 32 separates the lower ventricular region from the upper atrium region.

Generally, the left and right ventricles 12 and 14, respectively, each has a cavity 13 and 15, respectively, that is in fluid communication with cavities 17 and 19, respectively, of the atria (e.g., 16 and 18) through an atrioventricular valve 50 (which are each illustrated as being in the closed position in FIG. 2). More specifically, the left ventricle cavity 13 is in fluid communication with the left atrium cavity 17 through the mitral valve 52, while the right ventricle cavity 15 is in fluid communication with the right atrium cavity 19 through the tricuspid valve 54.

Generally, the cavities of the ventricles (e.g., 13 and 15) are each in fluid communication with the circulatory system (i.e., the pulmonary and peripheral circulatory systems) through a semilunar valve 44 (which are each illustrated as being in the open position in FIG. 2). More specifically, the left ventricle cavity 13 is in fluid communication with the aorta 26 of the peripheral circulatory system through the aortic valve 46, while the right ventricle cavity 15 is in fluid communication with the pulmonary artery 28 of the pulmonary circulatory system through the pulmonic valve 48.

Blood is returned to the heart 10 through the atria (e.g., 16 and 18). More specifically, the superior vena cava 22 and inferior vena cava 24 are in fluid communication with and deliver blood, as it returns from the peripheral circulatory system, to the right atrium 18 and its cavity 19. The pulmonary veins 30 are in fluid communication with and delivers blood, as it returns from the pulmonary circulatory system, to the left atrium 16, and its cavity 17.

The heart 10 is enclosed in the thoracic cavity within a double walled sac commonly referred to as the pericardium. Its inner layer is the visceral pericardium or epicardium, and its outer layer is the parietal pericardium. The heart 10 is generally made up of, among other materials, cardiac muscle or tissue 32, which has an exterior surface commonly known as the epicardial surface 34 and an interior surface, or endocardial surface 38, that generally defines the cavities (e.g., ventricular cavities 13 and 15, respectively, and atrial cavities 17 and 19, respectively). Coronary arteries 36 on the epicardial surface 34 of the heart 10 provide blood and nourishment (e.g., oxygen) to the heart 10 and its cardiac tissue 32.

By way of a non-limiting example, the present invention will be discussed in terms of embodiments that are used to primarily assist in the restructuring or reconfiguring, and/or operation of the left ventricle chamber (e.g., 12) of the natural heart 10. However, it is noted that the present invention can also be used to assist in the restructuring or reconfiguring, and/or operation of other portions of the natural heart 10, such as either atria (16 and/or 18), or the right ventricle chamber (e.g., 14).

Figure 3:
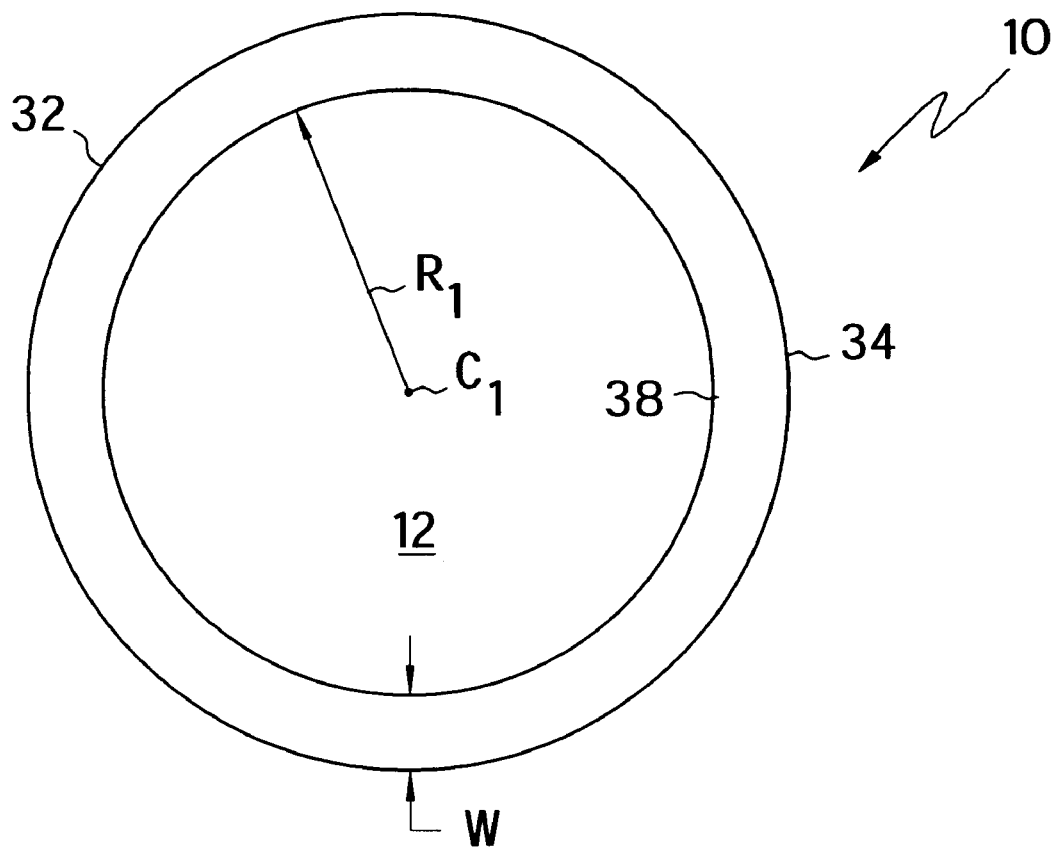
FIG. 3 is a horizontal cross sectional view of an unrestrained left ventricle of the natural heart.
Figure 4:
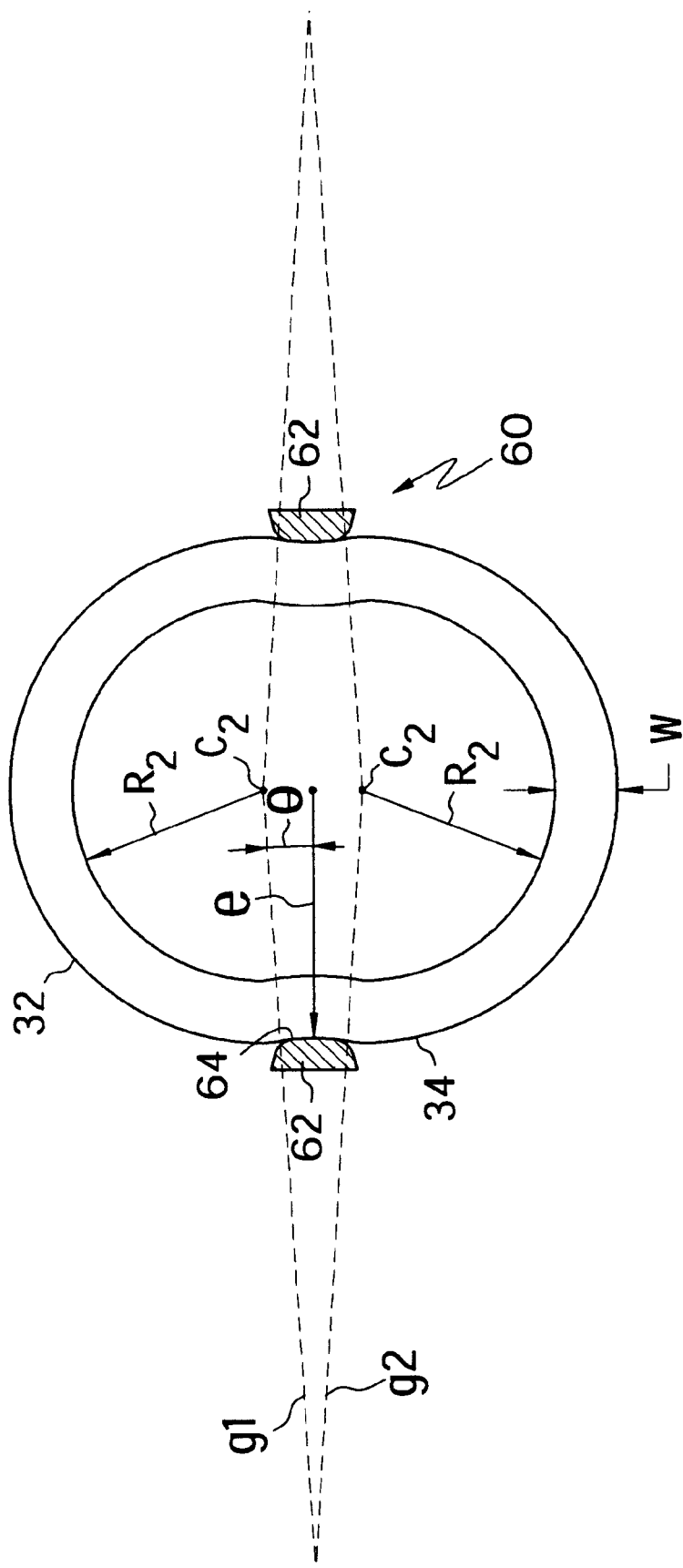
FIG. 4 is a horizontal cross sectional view of a heart restrained made in accordance with the present invention.

Turning now to FIG. 3, the chambers of the heart 10, including the left ventricle chamber 12, is generally shaped as a hollow truncated ellipsoid having, at any circular cross-section perpendicular to its long axis, a center point "$C_1$" and a radius "$R_1$" extending from center point $C_1$ to the endocardial surface 38. The cardiac tissue 32 of the heart 10 has athickness "w," which is generally the distance between the epicardial surface 34 and the endocardial surface 38.

The assembly 60 of the present invention exemplified in FIGS. 4 to 7 preferably is configured and positioned relative to the natural heart 10 to displace at least two portions of the cardiac tissue 32 inwardly (see, e.g., FIG. 4) from the unrestricted position, as exemplified in FIG. 3. By displacing portions of the cardiac tissue 32 inwardly, the shape of the chamber (e.g., the left ventricle chamber 12) of the heart 10 is generally restructured or reconfigured from a generally hollow truncated ellipsoid (see, e.g., FIG. 3) to a chamber generally shaped as having at least two continuous communicating portions of truncated ellipsoids (see, e.g., FIG. 4). In generally reconfiguring or restructuring the heart 10 as such, each of the truncated ellipsoids has an adjusted radius "$R_2$," which is preferably shorter than radius "$R_1$."

The assembly 60 can be static in that it does not actuate or pump the heart 10, but rather, displaces and holds portions of the cardiac tissue 32 in a generally predetermined fixed position as the heart 10 continues to contract (e.g., beat) and pump blood through its chambers and through the body's circulatory system. Nevertheless, the assembly 60 can be configured and constructed to permit torsional deformation as the natural heart 10 beats.

Figure 5:
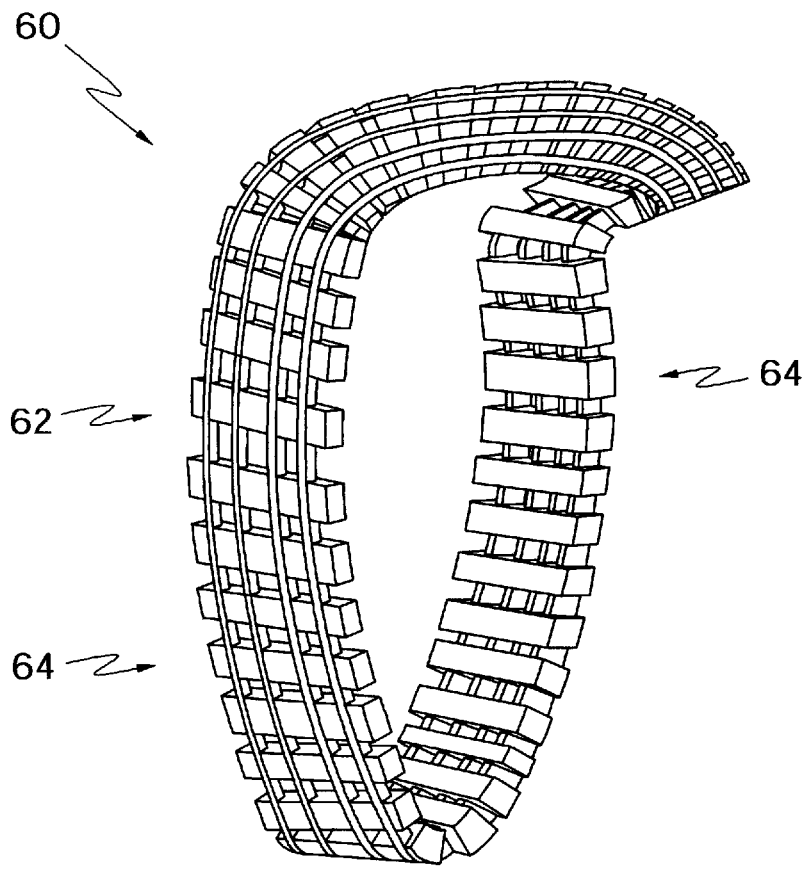
FIG. 5 is a perspective view of a device made in accordance with the present invention.
Figure 6:
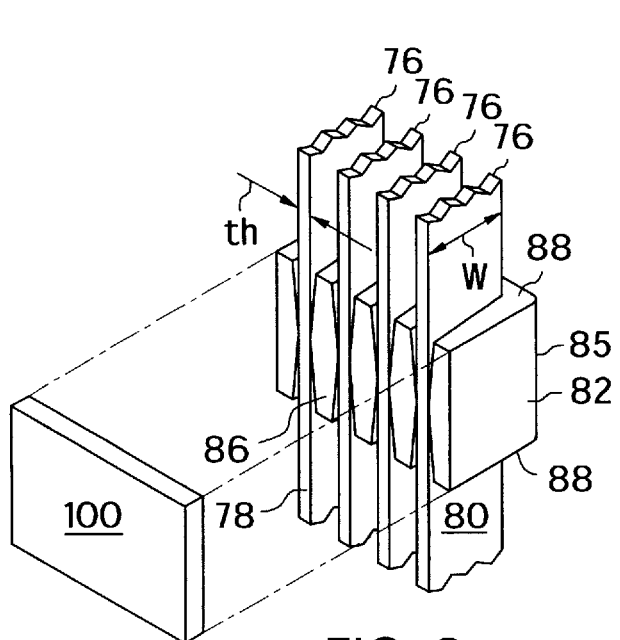
FIG. 6 is an enlarged exploded perspective view of a portion of the assembly made in accordance with the present invention.
Figure 7:
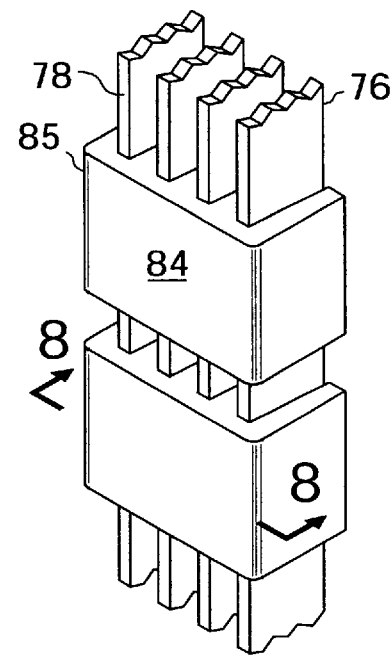
FIG. 7 is an enlarged perspective view of another portion of the assembly made in accordance with the present invention.
Figure 10:
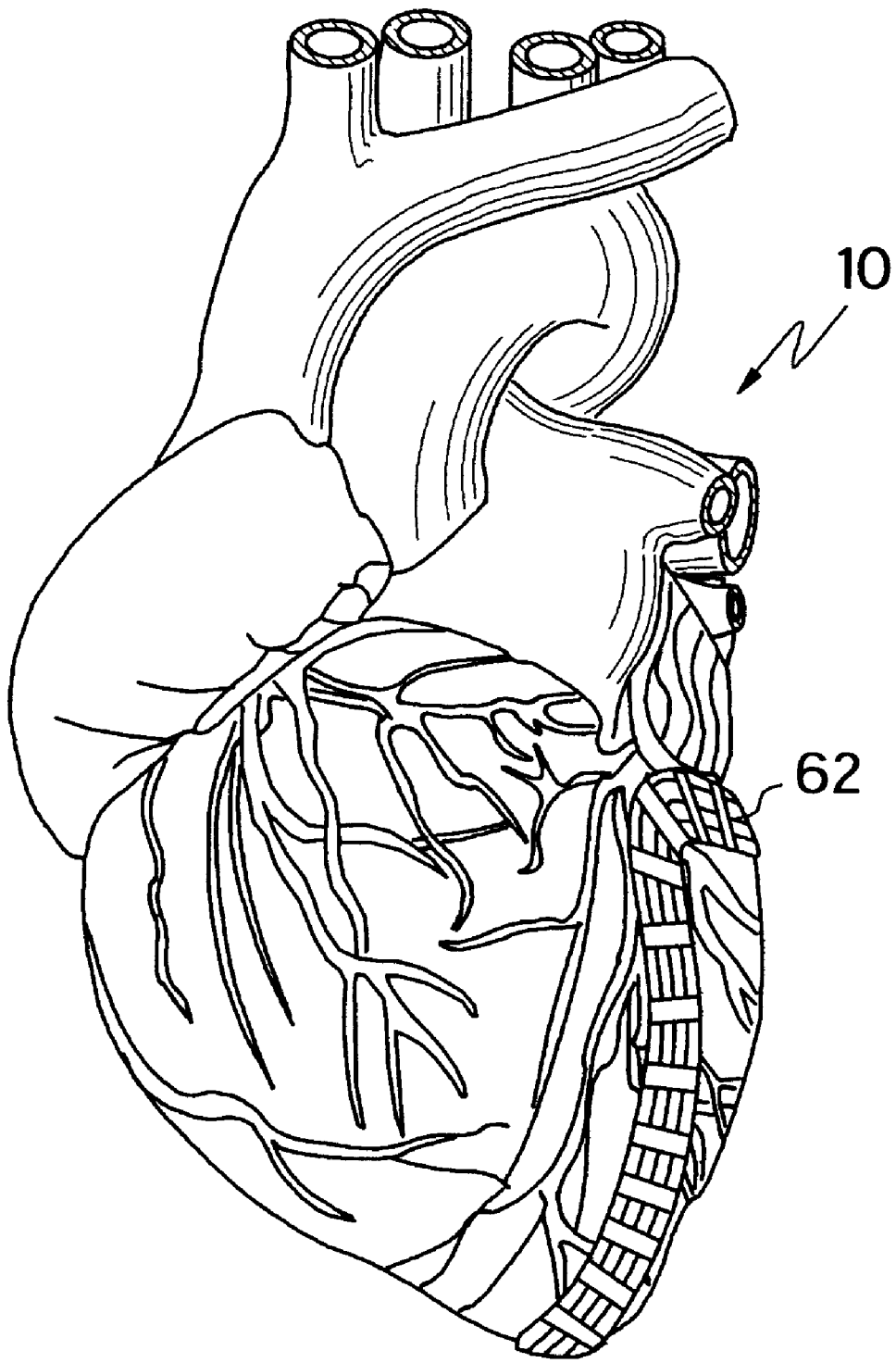
FIG. 10 is a perspective view of the assembly made in accordance with the present invention and positioned in the left ventricle.

The assembly 60 can include a yoke or collar 62, as exemplified in FIGS. 5–7, to assist in restraining or restructuring a ventricle, such as the left ventricle chamber 12. Collar 62 can be any desired shape and preferably surrounds or encircles the heart 10, and preferably one chamber (e.g., the left ventricle chamber 12) as best exemplified in FIG. 10, so as to restructure or reconfigure the left ventricle chamber 12 as having a shape approximating at least two continuous communicating portions of truncated ellipsoids. Preferably, a portion or region 64 of the collar 62 can extend along the longitudinal plane or along the longer axis of the chamber. Suitable locations on the epicardial surface 34 for the region 64 can include the basal portion near the atrioventricular groove 43 (see, e.g., FIG. 1) and apical portion 20 of the heart 10, the anterolateral surface of the left ventricle chamber 12, or the posteromedial surface of the left ventricle chamber 12.

The collar 62 may include two or more bands (e.g., 76) configured for positioning around the heart 10. Preferably, bands 76 are circumferentially flat and may be oriented with the surface 78 being positioned generally tangent to the epicardial surface 34 of the heart 10, and having the smaller dimension, as compared with surface 80. Surface 80 is generally oriented perpendicular to the epicardial surface 34. Band 76 should be sized so as to provide for low deformation in the direction perpendicular to the epicardial surface 34 of the heart 10, but only require a low strain energy for tortial deformation as the heart 10 beats. Band 76 can have a thickness "th" across surface 78 and a width "w" across surface 80, that each varies depending on the selected material and its particular deformation characteristics. When metallic material is used with the present invention, the band 76 can have a thickness "th" across surface 78 of about 0.2 mm, and can have a width, "w" across surface 80 from about 5 mm to about 12 mm, and more preferably, about 7 mm. It should be noted that the particular dimensions of each assembly 60, and of its components (e.g. collar 62 and its various portions, bands 76, etc.) will depend, as will be discussed later, according to particular anatomy, the desired application, and upon the particular size and configuration of the individual natural heart 10.

In constructing assembly 60 using bands 76, from about 2 to about 10 bands 76 may be used, and preferably about 4 bands 76 are used in the present invention. Nevertheless, the number of bands 76 may be selected dependent upon the property of the material selected for each of the bands 76, as well as the load stress required to appropriately restructure the heart chamber geometry.

Bands 76 are each preferably made of a light weight, generally rigid material that has a low bending strain under expected levels of stress so that the material has sufficient wear resistance in use while the heart 10 beats, and maintains its desired shape in use adjacent the heart 10. Illustrative examples of suitable materials which may be employed as bands 76 include any biocompatible or biomedical materials, such as metals, including titanium or stainless steel, or a suitable polymer, including polyacetal or an ultra high molecular weight polyethylene, or a combination of the same.

The collar 62 may preferably include a connector 82, and preferably a plurality of connectors 82 spaced along the collar 62, as exemplified best in FIG. 5. The connectors 82 can assist in maintaining the space relationship of the bands 76 relative to each other, and of the assembly 60 to the heart 10. Turning now to FIGS. 6–8, the connector 82 preferably has a contact or an inner surface 84, which is configured for placement adjacent or against the epicardial surface 34 of the natural heart 10. The inner surface 84 may be configured so that the epicardial surface 34 may slide along inner surface 84 during contraction and expansion of the heart 10, and to minimize damage to the epicardial surface 34, and the coronary arteries (e.g., 36). Preferably, the inner surface 84 is curved convex outwardly in a longitudinal plane (see, e.g., FIGS. 4 and 8) and has a smooth surface, and/or preferably rounded edges 87 so that collar 62 can be configured to be positioned adjacent or on the epicardial surface 34 whereby intimate contact can be established and maintained, even during the contraction or beating of the heart 10.

FIGS. 6–8 illustrate the connectors 82 as each including one or more grooves 92, which can extend inwardly from an opening 98 in the outer wall 86, and toward the contact or inner surface 84. Each groove 92 is preferably sized and configured to receive a band 76 whereby its surface 78 would be positioned adjacent the base wall 94, and its surfaces 80 preferably would be positioned adjacent sidewalls 96.

In an preferred embodiment, groove 92 should be configured to assist in allowing flexion movement of the band 76 as the heart 10 beats and moves. As best exemplified in FIGS. 6–8, grooves 92 may be tapered inwardly as the grooves 92 proceeds or extends from the outer surface 86 inwardly toward the contact surface 84. In addition, grooves 92 may also be tapered inwardly as the groove extends from each of the lateral surfaces 88 inwardly (e.g., upwardly and/or downwardly), as best illustrated in FIG. 6.

Connectors 82 are each preferably made of a light weight, generally rigid material that has a low bending strain under expected levels of stress so that the material has sufficient wear resistance in use while the heart 10 beats, and maintains its desired shape in use adjacent the heart 10. Illustrative examples of suitable materials which may be employed as connectors 82 may include any biocompatible or biomedical materials, such as metals, including titanium or stainless steel, or a suitable polymer, including polyacetal or an ultra high molecular weight polyethylene, or a combination of the same.

Turning back to FIG. 6, a structure 100 can be provided so as to assist in maintaining the bands 76 in the groove 92, in use. Any structure 100 contemplated for use with assembly 60 should assist in restricting movement of the band 76 out of the groove 92 through opening 98. In one embodiment, the structure 100 may take the form of a plate 100 that can be secured or otherwise attached, and preferably releasably secured, to close off or restrict access through one or more openings 98. In addition to a plate-like structure, sutures (not shown) may also be threaded through the connector 82 to assist in restricting bands 76 movement through opening 98. Structure 100 is preferably made of a biocompatible or biomedical material.

Turning now to FIGS. 11 and 12, an alternative embodiment of the present invention may include a collar or yoke 162 that provides an essentially continuous surface which contacts the epicardium surface 34 of the heart 10. In the present embodiment, collar 162 may take the form of a generally continuous yoke-like structure that is essentially rigid. Collar 162 preferably includes a contact or an inner surface 184, which is configured for placement adjacent or against the epicardial surface 34 of the natural heart 10. The inner surface 184 should be configured so that the epicardial surface 34 may slide along the inner surface 184 during contraction and expansion of the natural heart 10, and to minimize damage to the epicardial surface 34 and the coronary arteries (e.g., 36). Preferably, the inner surface 184 is curved convexly outwardly in a longitudinal plane and has a smooth surface, and/or preferably rounded edges 187 so that a collar 162 can be configured to be positioned adjacent or on the epicardial surface 34 whereby intimate contact can be established and maintained, even during the contraction or expansion of the natural heart 10.

The collar 162 preferably is selected from a generally rigid biomedical or biocompatable material. Examples of such suitable materials may include a metal, such as titanium or steel, or a polymer, such as an ultra high molecular weight polyethylene, polyacetal, or a polymer composite material such as carbon fiber-epoxy or fiberglass-epoxy, or a combination of the same. Moreover, the collar 162 may be covered, either partially or entirely, with a material that promotes tissue ingrowth into the collar 162, such as a soft tissue polyester fabric sheeting or polyletrafluroethyhere (PTFE).

Figure 13:
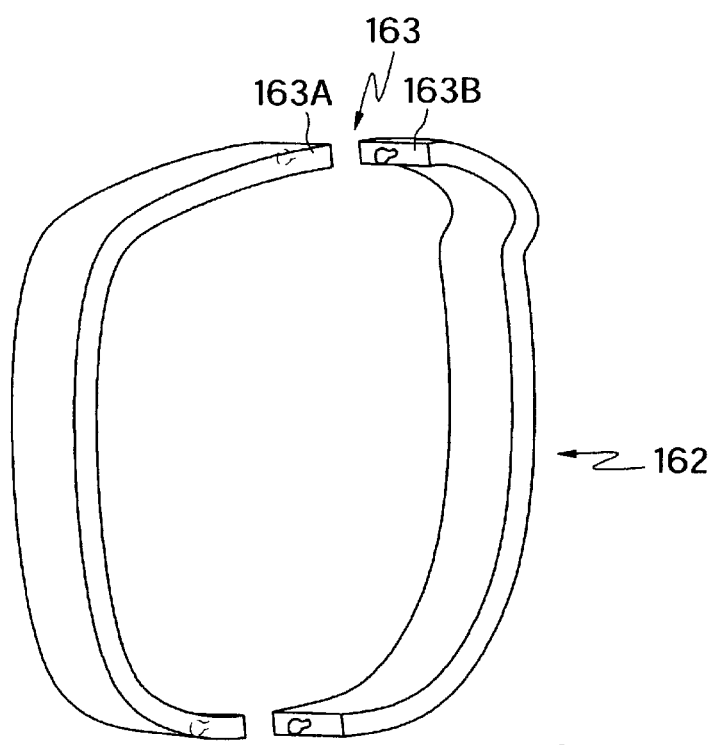
FIG. 13 is another alternative embodiment of the assembly made in accordance with the present invention.
Figure 14:
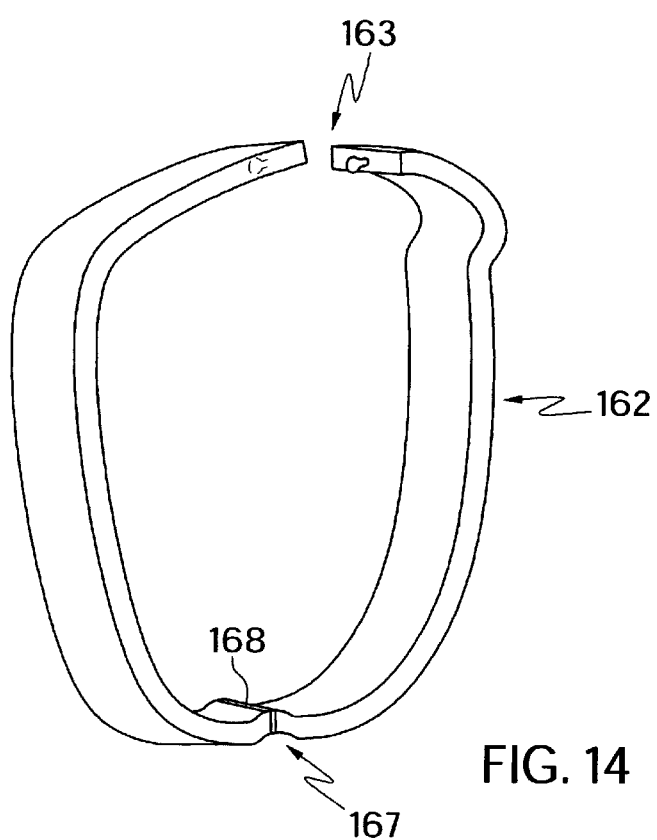
FIG. 14 is yet another alternative embodiment of the assembly made in accordance with the invention.

In other alternative embodiments, exemplified in FIGS. 13–14, it is contemplated that the collar 162 may include an attachment system 163 that allows the collar 162 to be placed around the heart 10, such as in between the pulmonary veins 30 near the basal portion of the heart 10 so as to reduce the possibility of lateral or medical displacement of the assembly 60, or about the lateral atrium or the atrioventrialar groove region. In one embodiment, the collar 162 may include an attachment system 163 that permits the collar 162 to be separated and then reattached at two or more sites or positions along the collar 162, preferably adjacent or near the region of the collar 162 configured for placement adjacent or on the basal portion and/or apical portion 20 of the natural heart 10. While the attachment system 163 is illustrated as an interlocking pin 163B and receptacle 163A (e.g., a ball and socket-like joint), it is contemplated, and as would be appreciated by those skilled in the art, other devices and assemblies for releaseably securing the collar 162 together can be used. Example of such devices and assemblies for attachment system 163 could include sutures, a screw and bore holes through overlapping portions of the collar 162, clamps, a combination of these devices and assemblies.

Alternatively, as illustrated in FIG. 14, the collar 162 may include an attachment system 163 at one site along the collar 162, preferably adjacent or at the portion of the collar 162 configured for placement adjacent on or the basal portion of the heart 10. This embodiment of collar 162 preferably would include a portion 167 that can either include flexible material or a pivotable section 168 to provide movement of the collar 162 so that the attachment assembly 163 can open, and the collar 162 can be slipped around the heart 10, and/or between the pulmonary veins 30.

Figure 15:
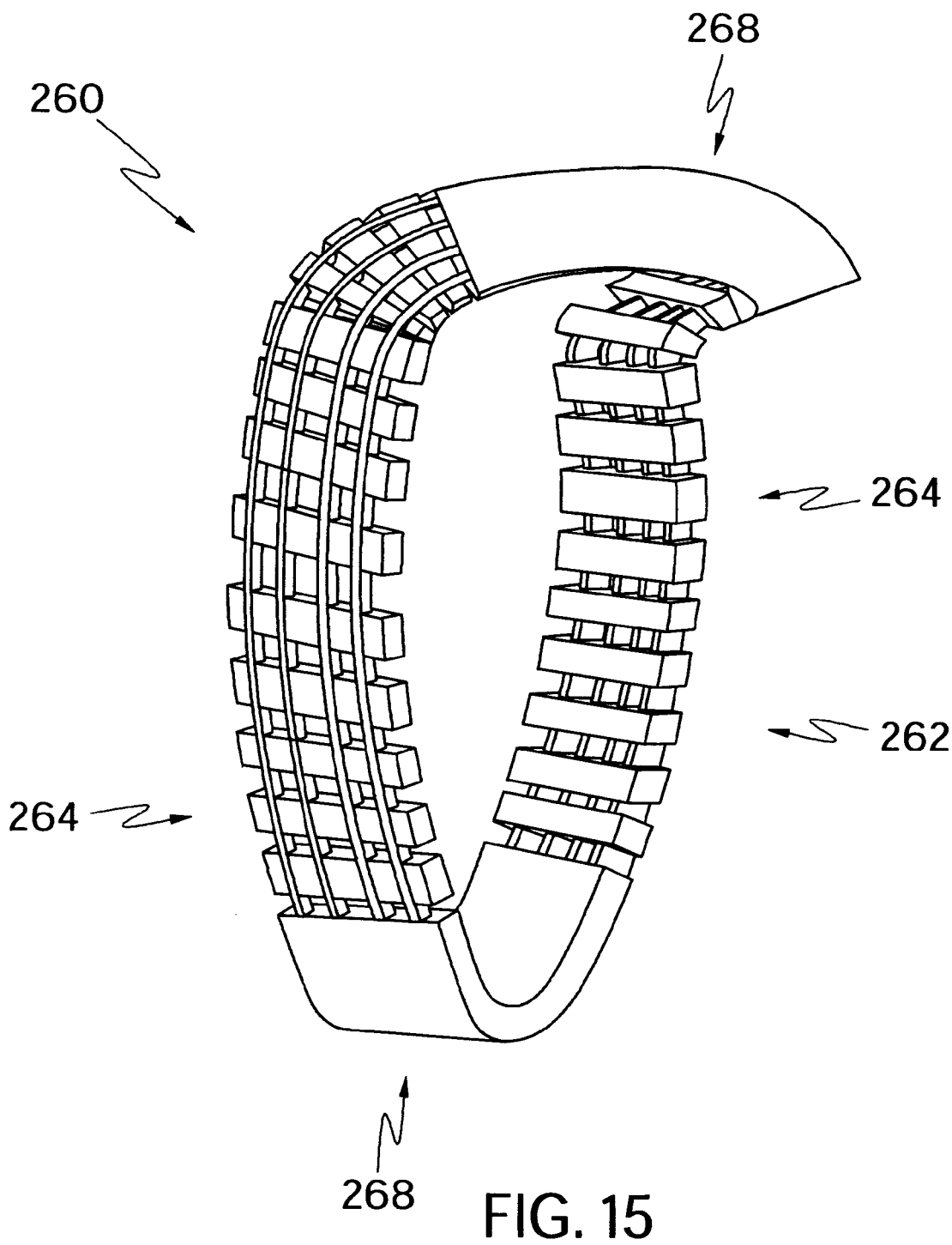
FIG. 15 is another alternative embodiment of the assembly made in accordance with the present invention.

In yet another embodiment illustrated in FIG. 15, the assembly 260 may include a collar 262 having a region 264 similar to the structure of the collar 62, exemplified above in FIGS. 4–8, and connector portions or regions 268, similar to the structure of the collar 162, discussed above, and exemplified in FIGS. 12–14.

To assist the epicardial surface 34 in separating from each of the collars 62, 162, or 262 adjacent or at the lateral portions 85 of inner surface 84 without creating substantial negative pressure, a pad 56 can be positioned and/or interposed between the epicardial surface 34 and the inner surface 84 of one or more of the connectors 82. Pad 56 can be, as exemplified in FIGS. 9A and 9B, a fluid-filled or gel-filled pad or cushion, which generally will occupy space laterally beyond the collar 62 and the lateral portions 85 of inner surface 84 while the heart 10 is in a relaxed state. However, as the heart 10 contracts and the wall shortens (see, e.g., FIG. 9B), generally circumferentially (reducing cavity radius), the epicardial surface 34 will "peel away" from the collar 62 and the lateral portions 85 of inner surface 84 and thus, fluid or gel in the pads 56 can fill this space so that the inner surface 84 and epicardial surface 34 remain in contact and effect focal restraint whereby the chamber 12 is restructured, as detailed above.

In one embodiment, the pad 56 is a closed system. Alternatively, it is contemplated that pad 56 can be configured such that fluid and/or gel can be added or removed to enhance functionality of the device assembly of the present invention, as desired. For example, one or more lines 58 can be in fluid communication with a chamber in pad 56. Line 58 can extend from pad 56 to an injection port 59, which can be positioned subcutaneous or elsewhere, as desired, for enhanced access. As will be appreciated by those skilled in the art, fluid or gel can be injected into the injection port 59 using a standard syringe and needle, or other device, to increase the size of the pad 56 and/or the pressure within the pad 56, as desired. Alternatively, fluid or gel can be withdrawn as desired.

Alternatively, pad 56 can be a low durometer polymer such as a plastic or other material (e.g., rubber). In use, as detailed above, the material accommodates and maintains the contact between the collar 62, and more specifically its inner surface 84, and epicardial surface 34 and thus, the desired reconfiguration of the heart 10 as the heart 10 beats or deforms.

Figure 16C:
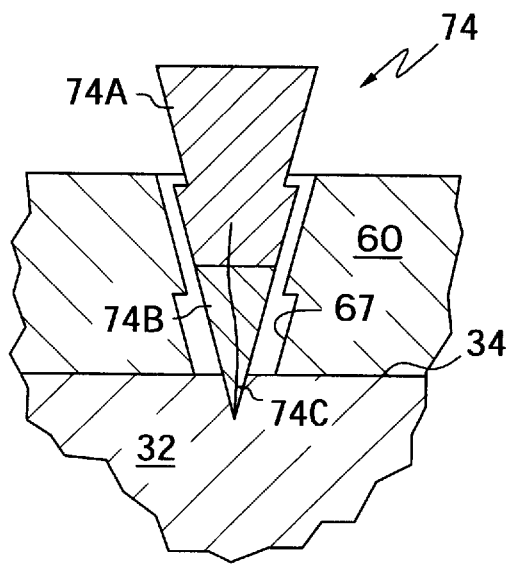
FIG. 16c is a vertical cross sectional view of the auxiliary connector of FIG. 16a made in accordance with the present invention.
Figure 17:
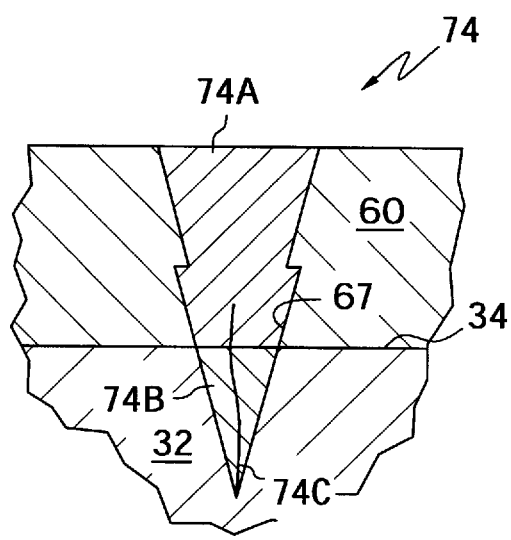
FIG. 17 is another vertical cross sectional view of the auxiliary fastener of FIG. 16c inserted into the assembly.
Figure 18:
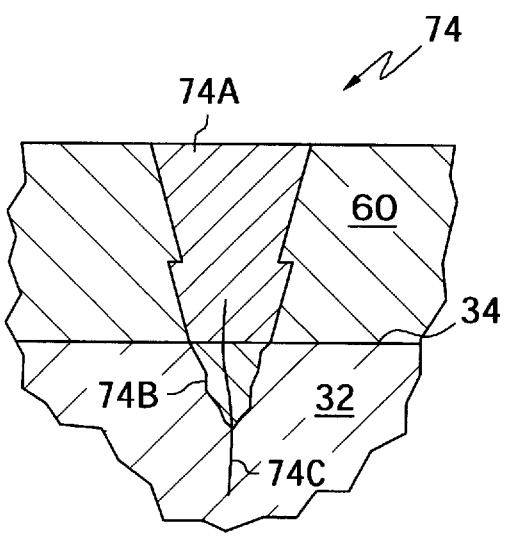
FIG. 18 the vertical cross sectional view of the embodiment of FIG. 16c illustrating the auxiliary connecter.
Figure 19:
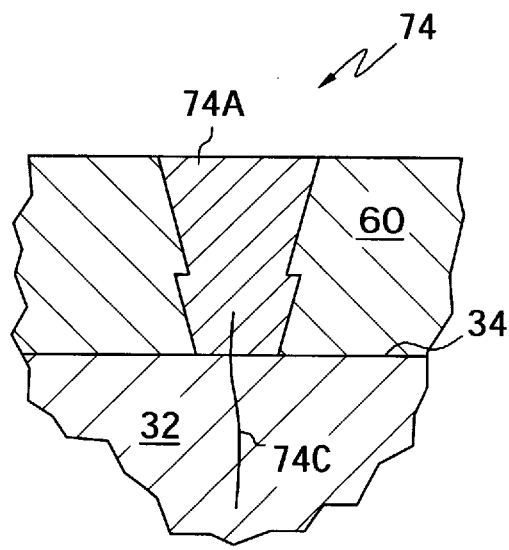
FIG. 19 is a vertical cross sectional view of the auxiliary fastener of FIG. 16c a period of time after being inserted into position.

To assist each of the assembly 60 in remaining fixed in a spatial or spaced relationship to each other and adjacent or on the epicardial surface 34, as desired, one or more auxiliary connectors 70 is provided. As shown in FIGS. 16a and 16b connector 70 can take the form of various mechanical connectors used in the industry to attach and position prosthetic devices in the body.

Auxiliary connector 70 can take the form of a spike shaped object or pin 71 that is configured to penetrate the epicardial surface 34 into the cardiac tissue 32. Also, auxiliary connector 70 can take the form of a button 72 and cord 73. One end of the cord 73 can be attached or otherwise secured to the collar 62, and it can extend inwardly into and through the cardiac tissue 32. A button 72 can be attached to or adjacent the other end of the cord outer wall 73 adjacent the endocardial surface 38. Button 72 can be made of any biocompatible material, and is preferably made of a material that enhances tissue growth around the button 72 to minimize the possibility of the formation of blood clots. It is further contemplated that other surgical attachment articles and techniques can be used in accordance-with the present invention, such as screws, surgical staples and the like, to assist in fastening and securing the assembly 60 in position, as desired.

Furthermore, auxiliary connector 70 can take the form of a peg 74, as exemplified in FIGS. 16a, 16b, 16c, and 17–19, that can configured to be lockably received in a hole 67 positioned and/or aligned on the assembly 60, and preferably on the connectors 82 or the collar 162. Peg 74 generally comprises a generally permanent potion 74A configured preferably to be snugly received in the hole 67, as discussed above. The portion 74A can be made of any suitable biomedical or biocompatible material. Suitable examples of materials for portion 74A, can include the same materials that can be used with the collar 62, as exemplified above.

At the end of the portion 74A of the peg 74, a generally rigid absorbable spike 74B is provided, which preferably is a generally fustoconicall shaped and tapers inwardly as the spike 74B extends away from the portion 74A. Spike 74B is sufficiently rigid so that it can pierce the tissue and then be inserted into the muscle tissue (e.g., the cardiac tissue 32). The material used for spike 74B should be a material that is absorbable by the body tissue over a period of time. Suitable materials can include a gelatin material, which can be partially denatured thermally or chemically to control solubility and the absorption rate in the tissue (e.g., 32), a polyglycol acid, or other materials, as will be appreciated by those skilled in the industry, used with absorbable surgical devices or sutures.

Within the portion 74A and spike 74B is a generally flexible extension 74C configured, for example, as a strip, coil, tube, or loop which preferably may include exposed interstices (mesh), holes, loops or other surface enhancements to promote tissue in growth. Extension 74C can be made from a material to enhance tissue integration therein. Suitable examples of materials for use as extension 74C can include polyester, polypropylene, and other polymers used in non-dissoluble implants.

In accordance with the teachings of the present invention, the assembly 60 should be so configured and positioned adjacent the heart 10 whereby the wall tension is reduced in accordance with LaPlace's theory of a chamber, which is as follows:

(Tension of wall)=(K*(chamber pressure)*(radius of chamber))/(wall thickness)

wherein K is a proportionality constant.

As an illustrative example of one embodiment in accordance with the teachings of the present invention, calculations will be performed based on the following model as exemplified in FIGS. 3 and 5. It is assumed that the long axis of the left ventricle 12 of the heart 10 is 100 mm, that the equatorial or short axis of the chamber 12 is 70 mm, that the equatorial wall thickness "w" of the chamber is about 10 mm and the basal diameter of the heart 10 is 60 mm. An arbitrary slice or plane of the left ventricle 12 will be analyzed to illustrate local dimensional computations for the present invention.

Furthermore, this model will assume that the inner radius "$R_1$" (of the slice or plane) of the unrestricted heart 10 (see, e.g., FIG. 3) is about 28.982 mm and that the heart 10 has an outer radius of about 38.406 mm. As is known to those skilled in the industry, the width "w" and radius "$R_1$" can be directly obtained from high-resolution imaging, such as an echocardiogram, or preferably, by computation based on an assumed geometric model. The ratio of the restraint contract pressure of the left ventricle 12 of the device 60 to the cavity pressure can vary from 1 to about 2. This example will further assume that the allowed ratio of the restraint contact pressure of the left ventricle 12 of device 60 to the cavity pressure is to be limited to a maximum of about 1.5, which is represented by symbol K in the mathematical formulas below. Also, it is desired to achieve an altered radius "$R_2$" of the left ventricle 12 to 80% of its original radius $R_1$, and as such:

$R_2 = 0.8 * R_1$ $R_2 = 0.8 * 28.982$ mm $R_2 = 23.186$ mm

In order to calculate the radius of curvature "g" of the inner surface 64 of member 62 in the transverse plane, the following formula can be used:

$g = (w + R_2) \div (k - 1)$ $g = (9.424$ mm $+ 23.186$ mm$) \div (1.5 - 1)$ $g = (32.61$ mm$) \div 0.5$ $g = 65.22$ mm.

Now that the value of radius of curvature of the inner surface 84 "g" has been calculated, the angle "θ" between the line $g_1$ (joining the center of curvature of the member 62 with one margin, in this plane, of the contact area between inner surface 84 and the epicardial surface 34) and line $g_2$ joining the same center of curvature with the center of the inner surface 84 in the same plane) can be calculated using the following formula:

$\theta = (\pi/2) * [R_2 - R_1] \div (R_2 + w + g)$ $\theta = (\pi/2) * [28.982$ mm $- 23.186$ mm$] \div (28.982$ mm $+ 9.424$ mm $+ 65.22$ mm$)$ $\theta = (\pi/2) * [5.796$ mm$] \div (103.636$ mm$)$ $\theta = 0.09063$ radius or 5.332 degrees Using the formula below, the distance inwardly that the heart 10 should be displaced can be calculated so that the desired restructuring can be achieved. If "e" is the distance that the center of either member 62 is to be separated from the absolute center of a remodeled ventricle in this plane, then:

$e = [(g + w + R_2) * \cos\theta] - g$ $e = [(65.22$ mm $+ 9.424$ mm $+ 23.186$ mm$) * \cos 5.332$ degrees$] - 65.22$ mm $e = 32.21$ mm.

As such, twice e or (2*e) is 64.42 mm, and this is the preferred distance separating the oppositely disposed inner surfaces 64.

Based on the calculation, the wall of the heart 10 needs to be displaced or moved inwardly about 6.20 mm from the unrestrained position to achieve the desired restructure or reconfiguration whereby wall tension is adjusted, as desired. Also, using the formula 2θg to calculate the desired contacting width of the inner surface 84, which is about 11.68 mm in this example.

To position the assembly 60 into a body (e.g., the thoracic cavity) and around an existing natural heart 10, a high resolution image, such as a standard echocardiogram, or other analysis of the heart 10 is preferred so that certain anatomical measurements can be electronically, preferably digitally, recorded and calculated, as detailed above. While the present application only includes one set of mathematic calculations to optimize the present invention, it is contemplated that measurements will need to be taken along several axes, planes, locations or positions along the longer axis of the chamber. Pre-surgical calculations are preferred so that the assembly 60 can be constructed, as desired, before surgery to minimize surgical time, and preferably reduce or eliminate use of a heart/lung bypass machine.

Thoracic surgery may be required to implant assembly 60. Clinically sufficient anesthesia is administered and standard cardiac monitoring is employed to the patient and then, via a sternal or lateral wall incision, the pericardial sac where the heart 10 is usually situated is opened using standard thoracic surgical procedures, which are known to those skilled in the art.

Once the thoracic cavity and pericardium is opened, the heart 10 must be narrowed or constricted so that the assembly 60 can be placed around the heart 10. In one embodiment, inflow to the heart 10 may be occluded. This can be accomplished by placing a tourniquet around either the superior and/or inferior vena cava 22 and 24, respectively, as illustrated respectfully in FIGS. 1 and 2, for a brief period of time (e.g., about 3 to 4 heartbeats) whereby the heart 10 shrinks and empties. Thereafter, the collar 62 may be slipped around the heart 10. The tourniquets can be released from occlusion around the superior and/or inferior vena cavas 22 and 24, respectively, and the heart 10 re-fills with blood.

While for prolonged reduction of blood pressure by cardiac inflow occlusion, hypothermia techniques may be employed to lower body temperature to reduce the side effects that can be caused by reduced blood pressure in the circulatory system.

If an open heart procedure employed in the present invention, circulation of blood to the natural heart 10 may be bypassed so the present invention can be inserted on and/or into the patient. If so, referring back now to FIG. 2, the superior vena cava 22, the inferior vena cava 24, and aorta 26 are cannulated. The circulatory system is connected to as a cardiopulmonary bypass machine so that circulation and oxidation of the blood are maintained during the surgical procedure. By way of example, the procedure discussed in detail will be for insertion of the present invention 60 to restructure or reconfigure the left ventricle chamber 12.

Turning now to FIGS. 4–7 and 10, assembly 60, which may have been customized according to the anatomical measurements and calculations, is preferably positioned adjacent or against the epicardial surface 34 in predetermined locations relative to each other and relative to the chamber (e.g., left ventricle chamber 12). Assembly 60 is positioned around the heart 10 so that portions of the heart 10 are displaced or urged inwardly, as desired.

Auxiliary connectors 70 can be used to further secure the assembly 60 to the heart 10.

Turning now to FIGS. 16–19, peg 74 can be inserted in the hole 67, whereby the spike 74B is piercing the epicardial surface 34 and is being inserted into the tissue (e.g., cardiac tissue 32).

Peg 74 preferably locks into position once inserted (see FIG. 17), to further secure the assembly 60 in place. Over time, it is preferred that spike 74B, which has been inserted into the tissue, dissolve and be absorbed by the surrounding tissue. As the spike 74B is being absorbed, extension 74C becomes exposed to the tissue, and tissue thereby insinuates and grows into any exposed interstices, loops, holes, or other surface enhancements to promote tissue ingrowth. The peg 74B can thereafter be held in place by the tissue insinuation and growth into extension 74C, which can assist in maintaining the position of assembly 60.

Once the assembly 60 is properly positioned and secured, termination of a cardiopulmonary bypass, if used, is attempted and, if successful, the thoracotomy is closed.

Alternatively, once the thoracic cavity and pericardium is open, the collar 162 exemplified in FIGS. 13 and 14, can be placed around the heart 10, either between the pulmonary artery 28 and the superior left atrial surface or between the aorta and the pulmonary artery 28 and then across the posterior dorsal left atrial surface in between the left and right pulmonary veins 30. A portion of the collar 162, preferably the posterior portion, can be placed behind the heart 10. An opening is sharply and/or bluntly developed in the leaves of the pericardium forming the anterolateral margin of the oblique sinus. Then, a hemostat can be used to place a portion of the collar 162 through the opening. Alternatively, a detachable cord, with one end attached to the portion of the collar 162, can be grasped and used to pull a portion of the collar 162 through the opening. Such placement of the collar 162 across the epicardial surface 34 of the lateral atrium or atrioventricular junction should reduce the possibility of adverse medial or lateral displacement or movement of the collar 162.

An alternative method for positioning the present invention includes removing the natural heart 10 from the patient, positioning all the components of the present invention assembly 60, as discussed above, and auto-transplanting the natural heart 10 back into the patient using standard cardiectomy and cardiac transplant techniques known in the industry.

Having shown and described the preferred embodiments to the present invention, further adaptations of the activation device for the living heart as described herein can be accomplished by appropriate modifications by one of ordinary skill in the art without departing from the scope of the present invention. For example, the present invention can be used with any one or even a plurality of the various chambers of a living heart, and also could be used with different structural embodiments to restructure the chamber. Several such potential modifications have been discussed and others will be apparent to those skilled in the art. Accordingly, the scope of the present invention should be considered in terms of the following claims and is understood not to be limited in the details, structure and operation shown and described in its specification and drawings.

I claim:

1. A geometric reconfiguration assembly for a natural heart, comprising:
   a collar configured for encircling an external surface of the natural heart in an unrestrained position and having a plurality of bands in a spaced relationship, the collar adapted to cause an inward displacement of at least one portion of the natural heart and to prevent the natural heart from returning to the unrestrained position at end diastole; and
   a connector bar intersecting the plurality of bands and configured for maintaining the spaced relationship of the bands to each other.

2. The assembly of claim 1, wherein the connector bar comprises an inner surface which is convex toward a surface of the natural heart.

3. The assembly of claim 1, wherein each of the plurality of bands are positioned parallel to each other.

4. The assembly of claim 1, wherein the assembly comprises from about 2 to about 10 bands.

5. The assembly of claim 1, wherein the bands comprise a high strength, high modulus polymer.

6. The assembly of claim 1, wherein the bands comprise a metal.

7. The assembly of claim 1, wherein the connector bar is positioned perpendicular to the plurality of bands.

8. The assembly of claim 1, wherein at least one of the bands has a thickness of about 0.2 mm.

9. The assembly of claim 1, wherein each of the bands includes a thickness, and the connector bar comprises a plurality of grooves configured to receive the thickness of each of the plurality of bands.

10. The assembly of claim 9, wherein the connector bar comprises at least one beveled groove.

11. The assembly of claim 1, wherein the connector bar comprises a cushioned portion.

12. The assembly of claim 1, wherein the connector comprises a closure device for enclosing at least one of the bands in the connector bar.

13. The assembly of claim 1, wherein the collar comprises a first restrictor region configured to be positioned adjacent the anterolateral surface of the heart and a second restrictor region configured to be positioned adjacent posteromedial surface of the heart.

14. The assembly of claim 11, wherein the cushioned portion comprises a polymeric material.

15. The assembly of claim 1, wherein said assembly comprises a pad provided adjacent the inner surface of the connector bar.

16. The assembly of claim 15, wherein the pad comprises a low durometer polymer.

17. The assembly of claim 15, wherein the pad comprises a cushion.

18. The device of claim 17, wherein the cushion comprises a gel-filled cushion.

19. The assembly of claim 17, wherein the cushion comprises a fluid-filled cushion.

20. A geometric reconfiguration assembly for a natural heart, comprising:
   a collar for encircling an external surface of a portion of the natural heart in an unrestrained position and adapted to cause an inward displacement of at least one portion of the natural heart and to prevent the natural heart frm returning to the unrestrained position at end diastole, said collar having a portion configred for placement on the basal portion of the natural heart between the left and right pulmonary veins, said collar further comprising an attachment assembly configured for releasably connecting said collar together,
   wherein the attachment system comprises a pin and receptacle, said pin and receptacle being releasably detachable.

21. A geometric reconfiguration assembly for a natural heart, comprising:
   a collar configured for encircling an external surface of a natural heart in an unrestrained position and adapted to cause an inward displacement of at least one portion of the natural heart and to prevent the natural heart from returning to the unrestrained position at end diastole, said collar having a first restrictor region for placement adjacent the anterolateral surface of the natural heart, and second rmstrictor region configured for positioning adjacent the posteromcdial surface of the heart; the first and second restrictor portions each coniprising a plurality of bands in a space relationship and a connector bar intersecting the plurality of band and configured for maintaining the space relationship of the bands to each other.

22. The assembly of claim 21, wherein the collar comprises a first connector portion configured for placement adjacent the basal portion of the heart and a second connector portion configured for a position adjacent the apical portion of the epicardium.

23. A method for reducing wall tension on at least one chamber of the natural heart, comprising the steps of
   providing a geometric reconfigutation assembly;
   encircling the external surface of at least one of the chambers of the natural heart in an unrestrained position, with said geometric reconfiguration assembly; and
   causing an inward displacement of at least one portion of the natural heart and preventing the natural heart from returning to the unrestrained position at end diastole, with said geometric reconfiguration assembly.

24. The method of claim 23, comprising the step of occluding blood inflow into the heart prior to placement of the assembly around the chamber of the heart.

* * * * *

UNITED STATES PATENT AND TRADEMARK OFFICE
CERTIFICATE OF CORRECTION

PATENT NO.   : 6,221,103 B1
DATED        : April 24, 2001
INVENTOR(S)  : David B. Melvin Page 1 of 1

It is certified that error appears in the above-identified patent and that said Letters Patent is hereby corrected as shown below:

Column 4,
Line 11, delete "gel-fiiled" and insert -- gel-filled --

Column 5,
Line 5, delete "perspcctive" and insert -- perspective --
Line 27, delete "finction" and insert -- function --

Column 6,
Line 31, delete "athickness" and insert -- a thickness --

Column 10,
Line 31, delete "outer wall"

Column 15,
Line 15, delete "frm" and insert -- from --
Line 16, delete "configred" and insert -- configured --

Column 16,
Line 3, delete "rmstrictor" and insert -- restrictor --
Line 4, delete "posteromcdial" and insert --posteromedial --
Line 5, delete "coniprising" and insert -- comprising --

Signed and Sealed this

Twenty-eighth Day of May, 2002

*Attest:*

*Attesting Officer*

JAMES E. ROGAN
*Director of the United States Patent and Trademark Office*

Adverse Decisions in Interference

Patent No. 6,221,103, Dr. David B. Melvin, DEVICE AND METHOD FOR RESTRUCTURING HEART CHAMBER GEOMETRY, Interference No. 105,450, final judgment adverse to the patentees rendered August 16, 2006, as to claims 23 and 24.

*(Official Gazette April 17, 2007)*